United States Patent [19]
Honkawa

[11] Patent Number: 5,469,987
[45] Date of Patent: Nov. 28, 1995

[54] CONTAINER WITH BAG DISPENSER

[75] Inventor: Bryan K. Honkawa, Venice, Calif.

[73] Assignee: Roll International Corporation, Los Angeles, Calif.

[21] Appl. No.: 214,948

[22] Filed: Mar. 16, 1994

[51] Int. Cl.⁶ ..................................... G07F 11/02
[52] U.S. Cl. .................. 221/96; 221/97; 221/199; 221/303; 221/305; 221/306
[58] Field of Search ................... 221/303, 305, 221/306, 307, 309, 96, 97, 199; 206/44.11, 45.12, 216, 233; 220/407, 908; 229/120.01, 122

[56] References Cited

U.S. PATENT DOCUMENTS

| | | | |
|---|---|---|---|
| 2,214,510 | 9/1940 | Robinson | 206/233 X |
| 2,457,107 | 12/1948 | Verner . | |
| 3,276,658 | 10/1966 | Locke | 229/120.01 |
| 3,542,259 | 11/1970 | Marchesani | 229/122 X |
| 3,982,659 | 9/1976 | Ross | 206/233 X |
| 4,019,635 | 4/1977 | Boots . | |
| 4,166,567 | 9/1979 | Beach, Jr. et al. . | |
| 4,296,860 | 10/1981 | Hsu et al. . | |
| 4,349,123 | 9/1982 | Yang . | |
| 4,363,405 | 12/1982 | Christie . | |
| 4,364,490 | 12/1982 | Lang et al. . | |
| 4,585,143 | 4/1986 | Fremow et al. . | |
| 4,648,530 | 3/1987 | Granger | 221/307 X |
| 4,666,064 | 5/1987 | Hoehn . | |
| 4,714,191 | 12/1987 | Richardson . | |
| 4,721,226 | 1/1988 | Yurko | 220/407 |
| 4,850,486 | 7/1989 | Niebaur . | |
| 4,850,506 | 7/1989 | Heaps, Jr. et al. . | |
| 4,850,507 | 7/1989 | Lemongelli et al. . | |
| 4,955,505 | 9/1990 | Battaglia . | |
| 4,993,318 | 2/1991 | Bollinger | 229/122 X |
| 5,109,978 | 5/1992 | Cawley . | |
| 5,301,833 | 4/1994 | Aycan | 221/307 X |

FOREIGN PATENT DOCUMENTS

| | | | |
|---|---|---|---|
| 578286 | 1/1994 | European Pat. Off. | 229/122 X |
| 53-66213 | 6/1978 | Japan | 206/216 X |

Primary Examiner—William E. Terrell
Assistant Examiner—Dean A. Reichard
Attorney, Agent, or Firm—William E. Thomson; Sean A. Luner

[57] ABSTRACT

A container with a built-in bag dispenser having one box comprising a bottom, four walls and a top. The first box has an opening for dispensing bags. Another box which also has four walls, a top and a bottom is attached to the interior of the first box. This second box contains bags and an opening for dispensing bags. A nozzle is used for dispensing the bags. A cover is attached to the nozzle in order to keep the bags sealed and clean.

20 Claims, 2 Drawing Sheets

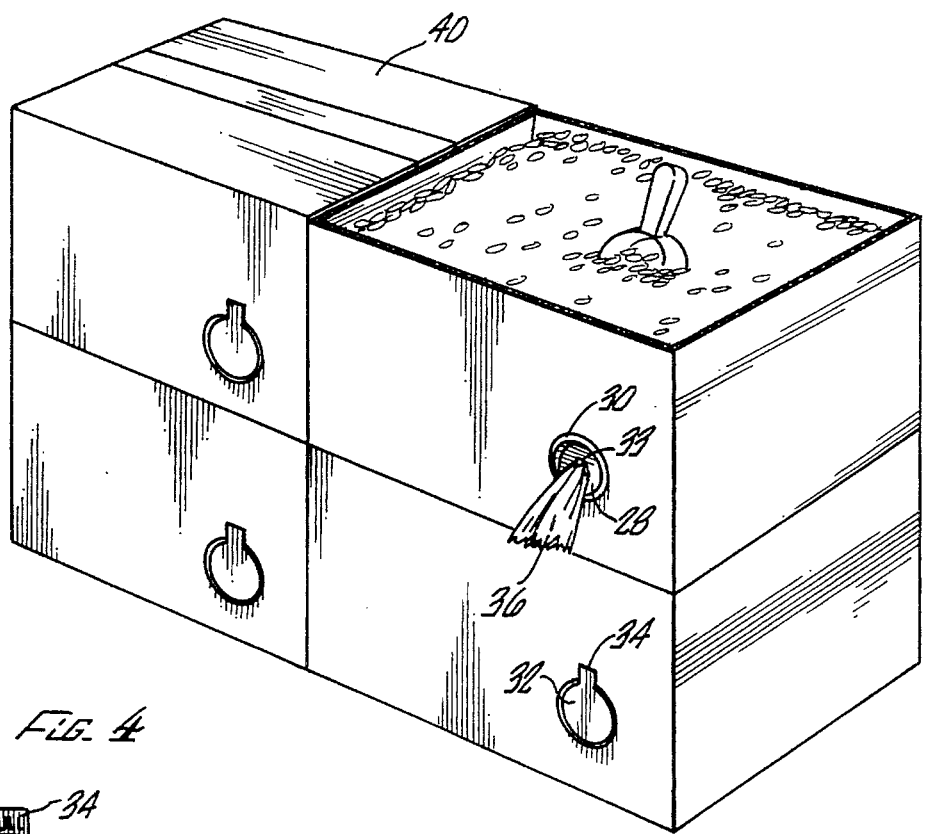
FIG. 4
FIG. 3
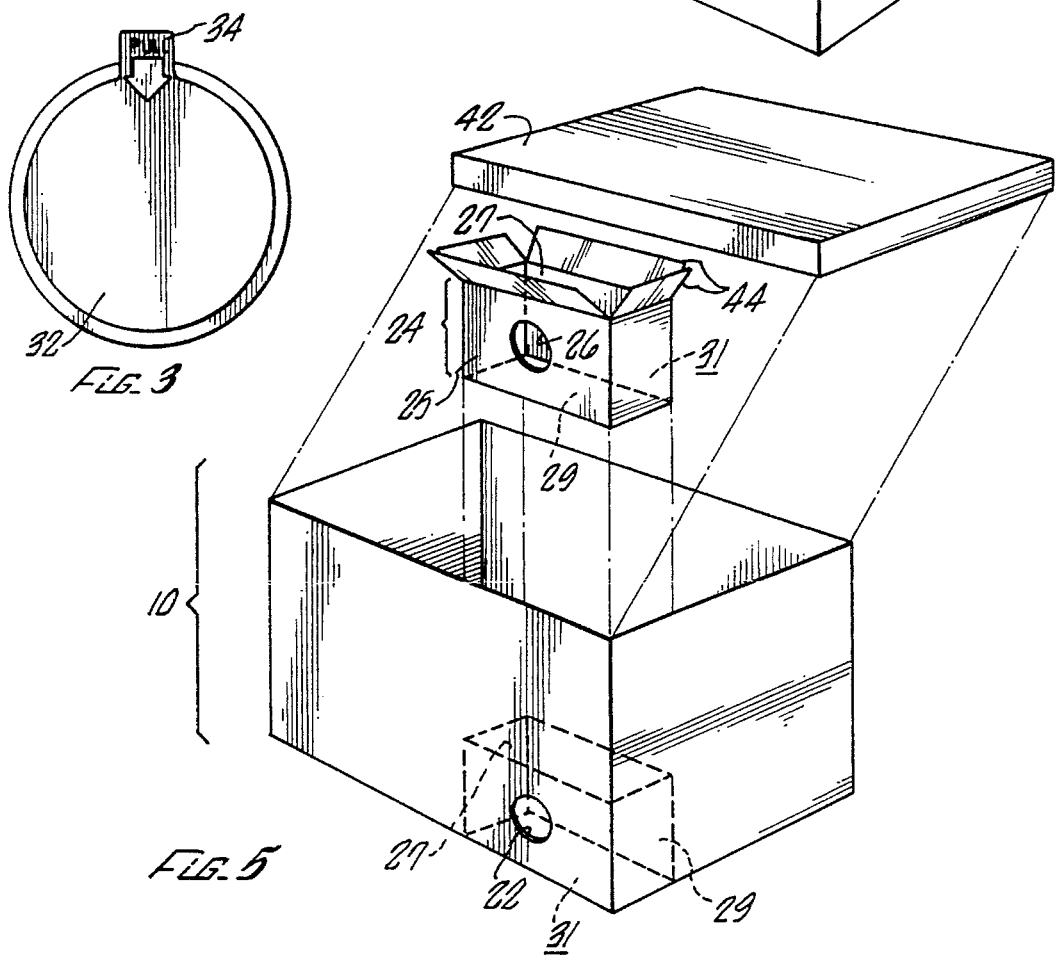
FIG. 5

CONTAINER WITH BAG DISPENSER

BACKGROUND OF THE INVENTION

This invention relates to a container with a bag dispenser.

Containers have become extremely common for a variety of uses. For example, containers are used for storage, shipping, display, dispensing, packaging as well as numerous other purposes. Containers exist in different sizes, shapes and colors. Containers are used in almost every industry for a variety of purposes.

Like containers, bags have also become extremely common for a variety of uses. Bags are used to store food, sell products, carry goods, collect trash, assist in medicine as well as other numerous uses. Bags can be paper, plastic or other suitable material. Bags also can be found in different sizes, shapes and colors.

With the above in mind, it is important to consider relevant art involving bags and containers. Bags and containers have been used for a variety of purposes. The following is a review of relevant art which involves containers, bags and bag dispensers.

Verner, U.S. Pat. No. 2,457,107, discloses a dispensing container adapted for use in dispensing gummed paper. The dispensing container is constructed from a single sheet of material. It is arranged to allow the gummed paper to be readily dispensed from the container. Christie, U.S. Pat. No. 4,363,405, discloses a plastic grocery bag dispensing carton. In particular, the dispensing carton is a disposable dispenser for use with a flexible film bag. These bags can be used by consumers as grocery bags or trash bags. The container supports the comparatively limp bag in an open condition so that the bag is ready to be used, i.e., loaded with grocery contents or trash. The dispensing container can also be used as a shipping container for the bags. It is a corrugated box with a wire clip arranged to double as a support for holding open and upright plastic bags one at a time.

Hoehn, U.S. Pat. No. 4,666,064 discloses a dispensing device for a "bag-in-box" package. This patent is directed towards a packaging system where a bag of flexible material is filled with a liquid product through a corresponding opening. It includes a dispensing device at the opening allowing liquid to be dispensed from the bag in the box. The bag is pulled through the dispensing opening of the dispensing device. The device is capable of firmly clamping the bag such that the bag and its contents can be sealed. The bag is contained within a stiff envelope such as a cardboard box. Most commonly liquids such as wine, fruit juice and edible oils are packaged in this manner.

Other relevant art, Heaps, Jr., et al., U.S. Pat. No. 4,850,506 discloses a container for large quantities of fluent material. This disclosure covers a container for shipment of large volumes of liquid materials in a multi-panel construction. A bag is contained within the multi-panel construction.

In addition to the above, other relevant art exists in which bags are enclosed within boxes. Fremow, et al., U.S. Pat. No. 4,585,143 discloses a liquid container with an internal bag. The Fremow patent includes tension straps for securing the container to a pallet for shipping. The construction of the container provides an extended discharge spout near the bottom of the bag. Boots, U.S. Pat. No. 4,019,635, discloses a pallet mounted, eight-sided container with internal plastic bag. It includes a sleeve nailed to the pallet and extending upwardly around the bottom of the bag. Beach, Jr., et al., U.S. Pat. No. 4,166,567 is an example of a container having multi-laminated walls of polygonal form with an internal bag. Still another example of a container formed of multi-walls from corrugated board with internal bag is Hsu et al., U.S. Pat. No. 4,296,860. This container is polygonal in form, mounted on a pallet and has an internal bag. This patent includes a specialized bottom construction for the container and its association with a shipping pallet.

Still other container and bag related constructions include trash containers with disposable bags. Lemongelli et al., U.S. Pat. No. 4,850,507 discloses a trash container with a box of folded disposable liner bags. The trash bag is replaced with a bag from the stored box of folded disposable liner bags at the bottom of the trash can. The disclosure is directed towards a container with a false bottom. The false bottom surrounds an opening through which folded bags are withdrawn. A bag containing box is secured in the false bottom of the trash can. The walls of the trash can contain tabs which retain the box in the false bottom and avoid unwanted removal.

Other dispensers of plastic bags include Cawley, U.S. Pat. No, 5,109,978. This patent discloses a dispensing receptacle for bags in a plastic bag roll. The invention includes a holder for plastic bag ties at one or on both of the sidewalls of the dispenser. The dispenser is mounted to a vertical surface using fasteners or mounted on a horizontal surface. The purpose of the invention is to hold and make available plastic bags for dispensing.

In addition to the above, other relevant art exists regarding plastic bag dispensers. U.S. Pat. No. 4,349,123 to Yang discloses a garbage can having a box-shaped dispenser as a bottom. The dispenser holds folded trash bags which are dispensed from a top mounted slot. Langet al., U.S. Pat. No, 4,364,490 discloses a trash receptacle having its bottom made out of a box-shaped dispenser. Rolled trash bags are complexly loaded into the dispenser and dispensed out of a top mounted slot. Richardson, U.S. Pat. No. 4,714,191 discloses flat cardboard that folds into a dispenser for plastic bags. The dispenser contains a top opening for dispensing the bags. The bags have tabs which interact with a tab on the dispenser to aid separation of the bags at the time of dispensing. U.S. Pat. No. 4,850,486 to Niebaur discloses a plastic bag dispenser shaped similar to a facial tissue box. The dispenser has a trash bag tie holder incorporated into it. Finally, U.S. Pat. No. 4,955,505 to Battaglia discloses a trash receptacle having its bottom made from a box-shaped dispenser for a spindle roll of trash bags. The bags dispense out of a top mounted slot.

SUMMARY OF THE INVENTION

Applicant has determined that it is useful to construct containers with built-in bag dispensers. Specifically, Applicant has determined that it is useful to construct shipping box containers which can be packed with goods and then converted to a bulk-bin container with a built-in bag dispenser. The container according to the present invention is structured to serve as a dispensing receptacle for particular goods in which bags can be used to facilitate sale or storage of such goods. While the relevant art offers a variety of structures relating to trash receptacles and plastic bag dispensers, the relevant art does not provide, teach or suggest a combination of shipping boxes which can be used as bulk-bin storage containers with built-in bag dispensers.

A non-limiting example of the advantages of the present invention includes use by grocery stores. A grocer cuts off the top of the shipping box and has a convenient method to sell goods with a built-in bag dispenser. The bags are used for holding the goods to be purchased. Prior to the Applicant's present invention such a combination did not exist. Grocers had to use plastic bag dispensers separate from the container with goods to be sold. The present invention is convenient and inexpensive to use.

The container according to the present invention is structured to serve as a shipping box, a dispensing receptacle for goods as well as a dispenser for bags. It can be used to dispense anything sold in bulk. This would include produce, candies, food stuffs, hardware and anything that could be sold out of a box. These are only examples and not meant to be limiting. In addition, the present invention might also be used for displays (permanent or temporary), display cards or pricing cards.

The container with a bag dispenser includes a first box with four walls, a bottom connecting the four walls and an open top. Each of the four walls are connected to a flap. The flaps are capable of folding inward, and closing the open top to form a top. The bottom can also be formed with flaps just as the flaps form the top. The bottom, walls and flaps form an interior space within the box. At least one of the four walls contains an opening for dispensing the bags.

A second box is located inside the interior space of the first box. The second box has four walls, a top and a bottom. The second box holds the bags to be dispensed. At least one of the four walls, the top or the bottom of the box contains an opening for dispensing bags. The second box is removably or permanently attached to the interior of the first box so that the opening in the first box and the opening in the second box are aligned for dispensing bags. The second box is preferably located against at least one of the four walls and resting on the bottom of the first box. In particular, the lower right or left corners would be preferred.

A nozzle is inserted into the openings of the first and the second box. The nozzle snaps into place and holds the second box in place. The nozzle has an opening and is capable of dispensing the bags. In addition, a cover can be placed over the nozzle to keep the bags clean and the contents sealed.

The container as used herein can be a storage box, shipping box, bulk bin or dispensing container. These are meant as examples only and are non-limiting. It can be constructed from corrugated cardboard or any other suitable material. Construction can be from one piece of material; i.e., dicut. Likewise the second box or bag dispenser can be constructed from corrugated cardboard or any other suitable material. It also can be constructed from one piece of material, i.e., dicut. One skilled in the art will be aware of what materials are suitable for the present invention.

The bags dispensed by the present invention can be mutually, serially joined in a severable manner and rolled into a roll, folded into a stack or filled into the second box. For example, the most preferred way to dispense bags is by using a bag roll. A bag roll contains bags serially connected together in the form of a roll. Each bag is capable of being separated from the next via perforated connections between them. These rolls have the advantage of providing a very compact volume of bags to be dispensed.

The second box can be removably or permanently attached to the interior of the first box by use of the nozzle for dispensing the bag, a front cover plate, glue, adhesive, snaps, rivets, staples or pins. One skilled in the art will recognize that almost any means of attachment can be used to keep the second box in place.

If the nozzle is to be used as a means of attachment the nozzle can be constructed such that its snaps into place inside of the dispensing holes of the first and second box. The nozzle can be constructed from plastic, or other suitable material. One skilled in the art will be aware of what materials are suitable for construction of the nozzle. It can be formed with a plurality of prongs which provide the snapping capability.

In another embodiment, the nozzle can be formed of 2 separate pieces. The first piece is a front cover plate which extends through both the opening in the first box and the opening of the second box. The front plate interacts with the nozzle, e.g. snaps into place, and holds the second box in place. The second piece of the nozzle is a dispensing nozzle. The front plate interacts with the nozzle, e.g. snaps into place, by using a plurality of prongs which snap into the dispensing nozzle. The dispensing nozzle contains openings which the prongs of the front plate can snap into to hold the second box in place. The dispensing nozzle can be attached at the opening of the second box. It extends into the interior of the second box. The dispensing nozzle has an opening through which it is capable of dispensing the bags within the second box. The bags can be pulled through the dispensing nozzle. The dispensing nozzle can be angled to provide better capability for dispensing the bags.

The present invention also can contain an outer cover. The outer cover is attached to the nozzle or front cover plate and seals the bags to be dispensed. Glue, staples, pins or adhesive can be used to attach the outer cover to the nozzle or front cover plate. The outer cover can be made of plastic, paper, tape or other suitable material. One skilled in the art will recognize what materials would be suitable. The outer cover can be releasably attached to the nozzle. The outer cover can also be permanently attached but capable of being opened for dispensing the bags. Preferably it contains adhesive for the purpose of releasable attachment.

In a different aspect of the present invention the walls of the first box may not contain the overlapping flaps. Instead a separate top can be used which covers the four walls and helps create the interior space within the first box. The top can be constructed such that it can be easily attached to the four walls for shipping purposes. In addition, the second box can be formed by using walls with flaps or by using a separate top as above.

In operation, a second box preloaded with a bag roll or stack of bags is placed into the first box prior to packing the contents to be shipped into the first box. The nozzle for dispensing is snapped into place and holds the second box in place. The outer cover can be placed over the nozzle to keep the bags clean and sealed. The contents can then be packed into the box and prepared for shipping to its destination. If a two piece nozzle is used, the prongs of the front cover plate are inserted into the openings of the first and second boxes and extend through the dispensing nozzle. The front cover plate prongs snap into place, (i.e., the prongs snap into the openings of the dispensing nozzle) and hold the second box in place.

Once received at the destination, the grocer, for example, cuts off the flaps connected to the four walls of the box such that the contents can be sold to the consumers. If the first box does not contain the four flaps the top is removed. The outer cover is taken off the nozzle or front cover plate and the bags exposed for dispensing. This system is easy to use and inexpensive.

Other features and advantages of the invention will be apparent from the following detailed description of the invention in conjunction with the accompanying drawings and from the claims.

BRIEF DESCRIPTION OF THE DRAWINGS

FIG. 3 is a drawing of the outer cover to be used with the nozzle or front cover plate.

FIG. 4 is a drawing of the container with separate and bag dispenser ready for use.

FIG. 5 is a drawing of the assembly of the container with separate top, and bag dispenser.

The drawings are not necessarily to scale, and certain features of the invention may be exaggerated and/or shown in schematic form in the interest of clarity and conciseness.

DETAILED DESCRIPTION OF THE INVENTION

Figure 1:
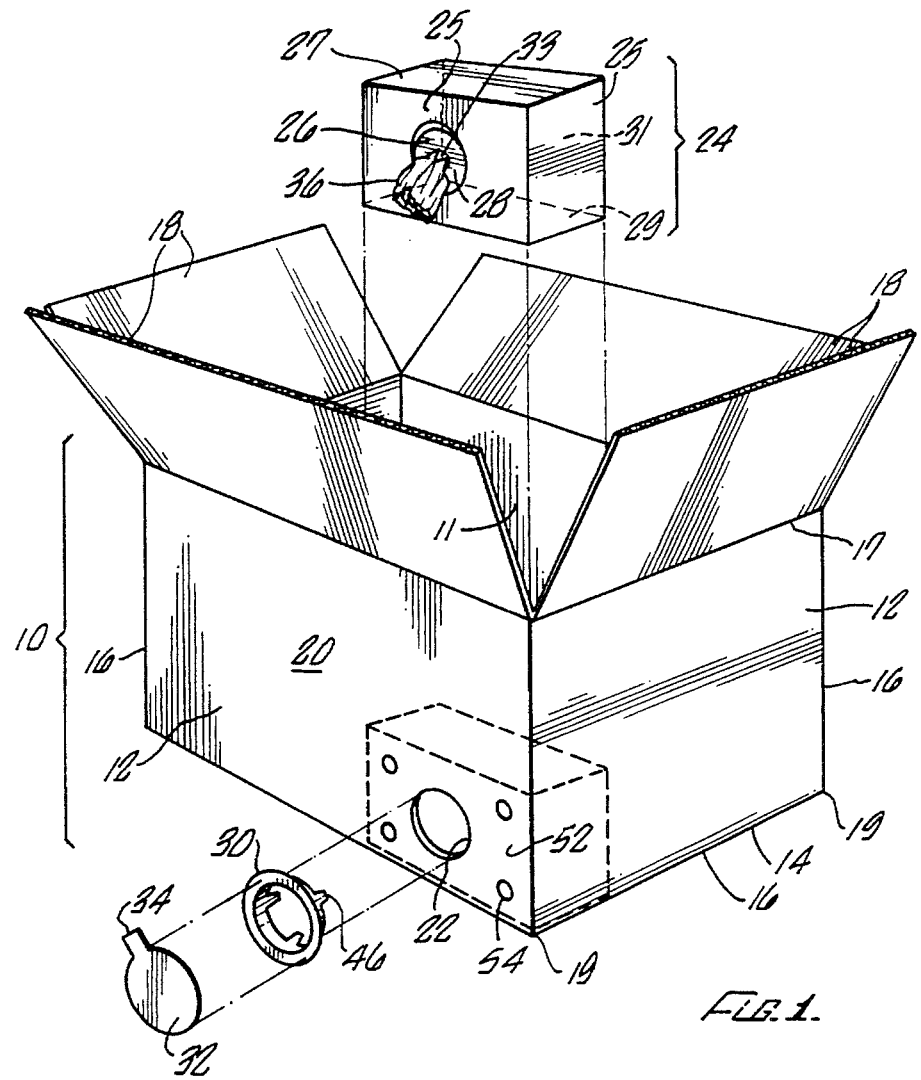
FIG. 1 is a drawing of the assembly of the container with bag dispenser.

Referring to the drawings, FIG. 1 generally shows the container 10. As can be discerned, the container 10 is composed of four walls 12 connected to a bottom 14 to form an open top 11. Each wall 12 is connected to an adjacent wall 12 and the bottom 14 at seams 16. Each wall 12 has a flap 18 capable of folding inward and/or outward over seams 17. When all four flaps 18 are closed an interior space 20 is formed. The bottom 14 can be formed the same way.

Located on at least one wall is an opening 22 for dispensing bags 36. The opening 22 can be placed anywhere within a wall 12. Preferably, the opening 22 is in the lower left, the middle or lower right hand corner of wall 12. The opening 22 is preferably positioned high enough above the bottom 14 to allow the second box 24 to rest on the bottom 14 such that opening 22 and 26 are aligned. The term "aligned" as used herein includes bringing into a line the two openings such that a bag can be passed through. The openings need not be aligned completely. If the opening 22 is located in the lower corners of wall 12, preferably the opening 22 is positioned also so the second box 24 will set adjacent to a corner 19. The dimensions of the opening 22 are large enough for bags 36 to be passed therethrough and dispensed.

It is preferred for the container 10 and second box 24 to be constructed of corrugated cardboard material. However the container 10 and second box 24 can be constructed out of plastic material or any other material suitable for shipping or dispensing goods. One skilled in the art will be knowledgeable on what materials can be used for the present invention. Construction can be in one piece, i.e., dicut.

FIG. 1 also shows a second box 24. The second box 24 is used for holding and dispensing the bags of the present invention. As can be discerned, the bag dispensing second box 24 is composed of four walls 25, a top 27 and a bottom 29. The four walls 25 are connected to the bottom 29 and top 27. When all four walls 25 are connected to bottom 29 an interior space 31 is formed. The bags to be dispensed can be inserted into this second interior space 31. Once the bags are within the second interior space 31, the top 27 can be connected to the four walls 25.

The second box 24 and the container 10 can be formed from one continuous piece, i.e., dicut or a number of pieces connected together. "Connected" as used herein refers to using tape, glue or other suitable material known to one skilled in the art so that the wall, top, bottom or flap to be connected can be attached or secured together. Connected can also include formation by one continuous sheet, i.e., dicut, of corrugated cardboard or other suitable material and creasing the cardboard at the point of connection.

The walls 25 of second box 24 can in another embodiment include flaps as in the first box (See FIG. 5). The four walls 25 are each connected to a flap 44. The flaps 44 are capable of folding inward or outward. When the flaps 44 are folded inward the flaps 44 close to form the top 27 and form the second interior space 31. The bottom 29 can also be formed the same way.

At least one of the walls 25, top 27 or bottom 29 contains an opening 26 for dispensing the bags 36. The opening 26 has a dimension so as to permit the bag 36 to be passed through and dispensed. A plastic nozzle 28 fits through the opening 26, extends into second interior space 31 and allows the bags 36 to be dispensed from second box 24. Nozzle 28 contains an opening 33 capable of dispensing the bags 36 from the second interior space 31.

In one embodiment, a front cover plate 30 is inserted through opening 22 and opening 26 and snaps in place, holds second box 24 in place and keeps openings 22 and 26 aligned. Front cover plate 30 is capable of fitting with dispensing nozzle 28 by using prongs 46 to help hold second box 24 in place. Prongs 46 snap into place. Nozzle 28 can be attached to the second box 24 with pins, glue, adhesive, staples or rivets. It is capable of receiving at opening 48 the prongs 46 of front cover plate 30 to help hold second box 24 in place. In addition, as shown in FIG. 1 second box 24 may also be held in place such that openings 22 and opening 26 are aligned by using glue 52, adhesive 52, pins 54, staples 54 or rivets 54 or other means as known to those skilled in the art. The front cover plate 30 and dispensing nozzle 28 can be constructed of plastic material and formed by an injection molding process. The front cover plate 30 and dispensing nozzle 28 can also be made of other suitable materials known to those in the art.

In another embodiment, the dispensing nozzle 28 and front cover plate 30 are all one piece. The one piece nozzle can be inserted into the openings 22 and 26 of the container 10 and second box 24. The one piece nozzle snaps into place using prongs 37 and holds the second box 24 in place. The one piece nozzle is capable of dispensing the bags 36 from the second interior space 31. The one piece nozzle has an opening 33 for dispensing the bags 36. The one-piece nozzle can also be used with pins, glue, adhesive, staples or rivets to hold the second box 24 in place.

Outer cover 32 is attached to the front of the front cover plate 30 in order to keep the bags clean and sealed. Outer cover 32 can be made from tape, paper, plastic or other suitable material known to one skilled in the art. The outer cover 32 is preferably attached to the front cover plate 30 by using adhesives. The outer cover 32 can be releasably or permanently attached to the front cover plate 30.

Figure 2:
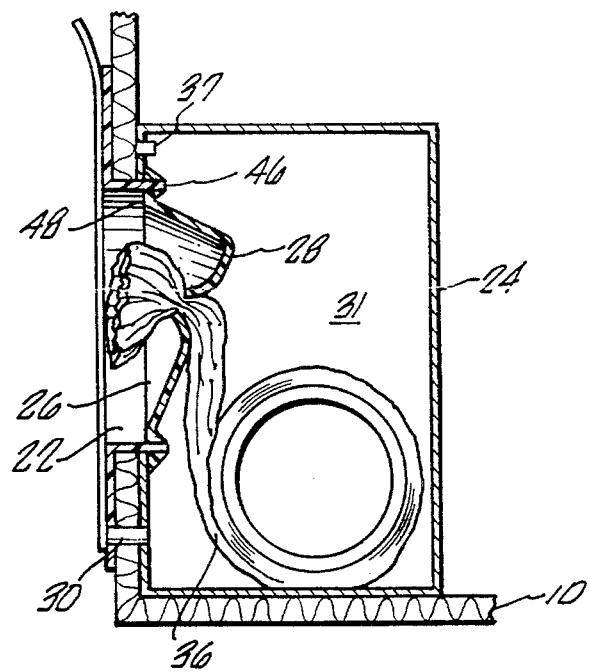
FIG. 2 is a side view drawing of the second box dispensing the bags, nozzle, front cover plate and outer cover as used in the present invention.

FIG. 2 shows generally the attachment of the second box 24 to the container 10 using a nozzle 28. As can be discerned, the front cover plate 30 is inserted through opening 26 and opening 22. The prongs 46 of front cover plate snaps in place into the openings 48 of dispensing nozzle 28, holds second box 24 in place, and keeps openings 22 and 26 aligned. Front cover plate 30 coordinates with dispensing nozzle 28 to hold second box 24 in place. Nozzle 28 can be attached to second box 24 at opening 26. Nozzle 28 extends through opening 26 and is capable of dispensing bags contained within the second interior 31 of second box 24 through an opening 33 in nozzle 28. Nozzle 28 can be angled so as to allow bags 36 to be dispensed easily. Nozzle 28 allows bag 36 to be dispensed through openings 22 and 26. As described above, glue, rivet, adhesive, staples and/or pins or other suitable means can be used to attach nozzle 28 to second box 24. A one piece nozzle is similar to the front cover plate 30 and nozzle 28 with snaps 37 holding second box 24 and container 10 in place.

FIG. 2 also shows the outer cover 32 releasably attached to the front cover plate 30. As seen in FIG. 3, the outer cover 32 has an upward tab 34 used in releasing the attached outer cover 32 from the front cover plate 30 by pulling tab 34 away from front cover plate 30. The outer cover 32 can also be permanently attached.

Referring now to FIG. 4, this drawing generally shows the shipping box or container 10 as used for dispensing goods with the built-in bag dispenser. As can be discerned, a person using the shipping box can cut the top 40 off container 10 in order to convert the shipping box to a bulk-bin. Customers can then obtain bags 36 from the built-in bag dispenser of second box 24 to hold the contents to be purchased from the bulk-bin of container 10. Bag 36 is dispensed through opening 33 in dispensing nozzle 28 or the one-piece nozzle. Prior to dispensing bag 36, seal 32 is removed from the front cover plate 30 by pulling tab 34 away from front cover plate 30. The shipping boxes can be stacked as shown in FIG. 4.

Now referring to FIG. 5, this drawing displays container 10 without flaps 18. Instead, a separate top 42 is used to cover the container 10. In addition, FIG. 5 displays a second box 24 without a top but instead flaps 44 connected to each of the four walls 25. The flaps 44 close the top 27 as described above for container 10. One skilled in the art will realize that any combination of a box with four walls, a top and bottom will work in the present invention. This includes any dimension, size, shape or construction (i.e., made from numerous pieces of material or made from one continuous piece). The boxes, sizes and shapes can be interchanged so long as the spirit of the invention is retained.

One skilled in the art will readily appreciate that the present invention is well adapted to carry out the objects and obtain the ends and advantages mentioned, as well as those inherent therein. Changes therein and other uses will occur to those skilled in the art which are encompassed within the spirit of the invention as defined by the scope of the claims. It will be readily apparent to one skilled in the art that bearing substitutions and modifications may be made to the invention disclosed herein without departing from the scope and spirit of the invention.

All patents and publications mentioned in this specification are indicative of the levels of those skilled in the art to which the invention pertains.

I claim:

1. A container with a bag dispenser comprising:

a first box comprising a bottom, four walls and a top forming a first interior space wherein at least one of said four walls contains a first opening for dispensing bags therethrough;

a second box comprising four walls, a top and a bottom forming a second interior space, wherein at least one of said four walls, said top or said bottom contains a second opening for dispensing bags therethrough; and a means for attaching said second box to said first box within said first interior space such that said first opening and said second opening are aligned.

2. The container of claim 1 wherein each of said four walls of said first box is connected to a flap capable of folding inward to form said top and said first interior space.

3. The container of claim 1 wherein said top of said first box is separate and removable from said bottom of said first box and said four walls of said first box.

4. The container of claims 1, 2 or 3, wherein said means for attaching said second box to said first box is selected from the group consisting of a nozzle, a front cover plate, glue, rivets, pins, staples, adhesive or tape.

5. A container with a bag dispenser comprising:

a first box comprising a bottom, four walls and a top forming a first interior space wherein at least one of said four walls contains a first opening for dispensing bags therethrough;

a second box comprising four walls, a top and a bottom forming a second interior space, wherein at least one of said four walls, said top or said bottom contains a second opening for dispensing bags therethrough; and a means for attaching said second box to said first box within said first interior space such that said first opening and said second opening are aligned and a nozzle extending through said first opening and said second opening to hold said second box in place within said first box, said nozzle containing an opening capable of dispensing bags from said second interior space.

6. The container of claim 4 further comprising bags which are mutually, serially joined in a severable manner and rolled into a roll, folded into a stack, or filled into said second interior space.

7. The container of claim 5, wherein said nozzle comprises a plurality of prongs capable of holding said nozzle in place and said second box in place.

8. The container of claims 1, 2 or 3 further comprising an outer cover removably or permanently attached to a container wall of said first box at said first opening.

9. The container of claim 8, wherein said outer cover comprises plastic or paper with adhesive, glue or tape to seal said first opening.

10. The container of claims 1, 2 or 3 wherein in said first and said second box are constructed from corrugated cardboard.

11. A container with a bag dispenser comprising:

a first box comprising a top, a bottom and four walls forming a first interior space, wherein at least one of said four walls contains a first opening for dispensing bags therethrough;

a second box comprising four walls, a top and a bottom forming a second interior space, wherein at least one of said four walls, said top or said bottom contains a second opening for dispensing said bags therethrough;

a dispensing nozzle for dispensing said bags, wherein said dispensing nozzle extends into said second interior space and said dispensing nozzle contains an opening capable of dispensing bags from said second interior space; and a means for attaching said second box to said first box within said first interior space such that said first opening and said second opening are aligned.

12. The container of claim 11 wherein each of said four walls of said first box is connected to a flap capable of folding inward to form said top of said first box and said first interior space.

13. The container of claim 11 wherein said top of said first box is separate and removable from said bottom and said four walls.

14. The container of claims 11, 12 or 13, wherein said means for attaching said second box to said first box is selected from the group consisting of a front cover plate, glue, rivets, pins, staples, adhesive or tape.

15. The container of claim 14, wherein said means for attaching said second box to said first box is a front cover plate comprising a plurality of prongs extending through said first and said second opening and interacting with said dispensing nozzle to hold said second box in place.

16. The container of claims 11, 12 or 13 wherein said dispensing nozzle is attached to said second box.

17. The container of claim 14 further comprising bags which are mutually serially joined in a severable manner and rolled into a roll, folded into a stack, or filled into said second box.

18. The container of claims 11, 12 or 13 further comprising an outer cover removably or permanently covering said first opening.

19. The container of claim 18, wherein said outer cover comprises plastic or paper with adhesive, glue or tape to seal said nozzle.

20. The container of claim 5 further comprising an outer cover removably or permanently covering said opening of said first box.

* * * * *